US012484912B2

(12) United States Patent
Haskell, Jr.

(10) Patent No.: US 12,484,912 B2
(45) Date of Patent: Dec. 2, 2025

(54) GARMENT TORNIQUET DEVICE

(71) Applicant: Todd Haskell, Jr., Hayward, WI (US)

(72) Inventor: Todd Haskell, Jr., Hayward, WI (US)

( * ) Notice: Subject to any disclaimer, the term of this patent is extended or adjusted under 35 U.S.C. 154(b) by 210 days.

(21) Appl. No.: 18/399,012

(22) Filed: Dec. 28, 2023

(65) Prior Publication Data

US 2025/0213254 A1 Jul. 3, 2025

(51) Int. Cl.
*A61B 17/132* (2006.01)
*A61B 17/00* (2006.01)

(52) U.S. Cl.
CPC *A61B 17/1327* (2013.01); *A61B 2017/00681* (2013.01); *A61B 2017/00862* (2013.01)

(58) Field of Classification Search
CPC .............. A61B 17/132; A61B 17/1322; A61B 17/1327; A61B 2017/00681; A61B 2017/00862; A41D 1/00; A41D 1/06
See application file for complete search history.

(56) References Cited

U.S. PATENT DOCUMENTS

| | | | |
|---|---|---|---|
| 2,702,551 | A | 2/1955 | Hobson |
| 7,604,651 | B1 | 10/2009 | Harris |
| 7,981,135 | B2 | 7/2011 | Thorpe |
| D818,670 | S | 5/2018 | Silvestre |
| 11,160,560 | B2 | 11/2021 | Rose |
| 2012/0158041 | A1 | 6/2012 | Craig |

FOREIGN PATENT DOCUMENTS

| | | |
|---|---|---|
| WO | WO2008076821 | 6/2008 |
| WO | WO2009029240 | 3/2009 |

*Primary Examiner* — Ryan J. Severson

(57) ABSTRACT

A garment tourniquet device includes a pair of pants that has a pair of legs and a pair of channels each integrated into each of a respective one of the pair of legs. A pair of tourniquets is each positioned in the channel in a respective one of the pair of legs of the pair of pants. A respective one of the pair of tourniquets is pullable into a tightened condition to tighten around the femoral artery in the respective user's leg thereby inhibiting the arterial bleeding in the user's respective leg. A pair of clasps is each attached to a respective one of the pair of tourniquets. A respective one of the pair of tourniquets is wrapped around the clasp to for retaining the respective tourniquet in the tightened condition.

13 Claims, 6 Drawing Sheets

GARMENT TORNIQUET DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to tourniquet devices and more particularly pertains to a new tourniquet device for quickly applying a tourniquet to a user's legs. The device includes a pair of pants and a pair of tourniquets each slidably integrated into a respective one of a pair of legs of the pair of pants and a pair of clasps attached to a respective one of the pair of tourniquets. Each of the tourniquets can be pulled into a tightening condition to compress the femoral artery in a respective user's leg. Additionally, each of the tourniquets can be wrapped around a respective clasp for retaining a respective tourniquet in the tightened condition to inhibit arterial bleeding in the user's respective leg in the event of a severe injury.

(2) Description of Related Art Including Information Disclosed Under 37 CFR 1.97 and 1.98

The prior art relates to tourniquet devices including a variety of garment tourniquet devices that each at least includes a pair of pants and a pair of tourniquets each attached to an outside surface of a respective one of a pair of legs of the pair of pants and a tactical garment device including a pair of pants and ballistic protection elements and a firearm attachment element and tourniquets integrated into legs of the pair of pants. In no instance does the prior art disclose a garment tourniquet device that includes a pair of pants and a pair of tourniquets each slidably integrated within a respective leg of the pair of pants and a pair of clasps each attached to a respective tourniquet such that the respective tourniquet can be wrapped around a respective clasp when the tourniquet is tightened.

BRIEF SUMMARY OF THE INVENTION

An embodiment of the disclosure meets the needs presented above by generally comprising a pair of pants that has a pair of legs and a pair of channels each integrated into each of a respective one of the pair of legs. A pair of tourniquets is each positioned in the channel in a respective one of the pair of legs of the pair of pants. A respective one of the pair of tourniquets is pullable into a tightened condition to tighten around the femoral artery in the respective user's leg thereby inhibiting the arterial bleeding in the user's respective leg. A pair of clasps is each attached to a respective one of the pair of tourniquets. A respective one of the pair of tourniquets is wrapped around the clasp to for retaining the respective tourniquet in the tightened condition.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
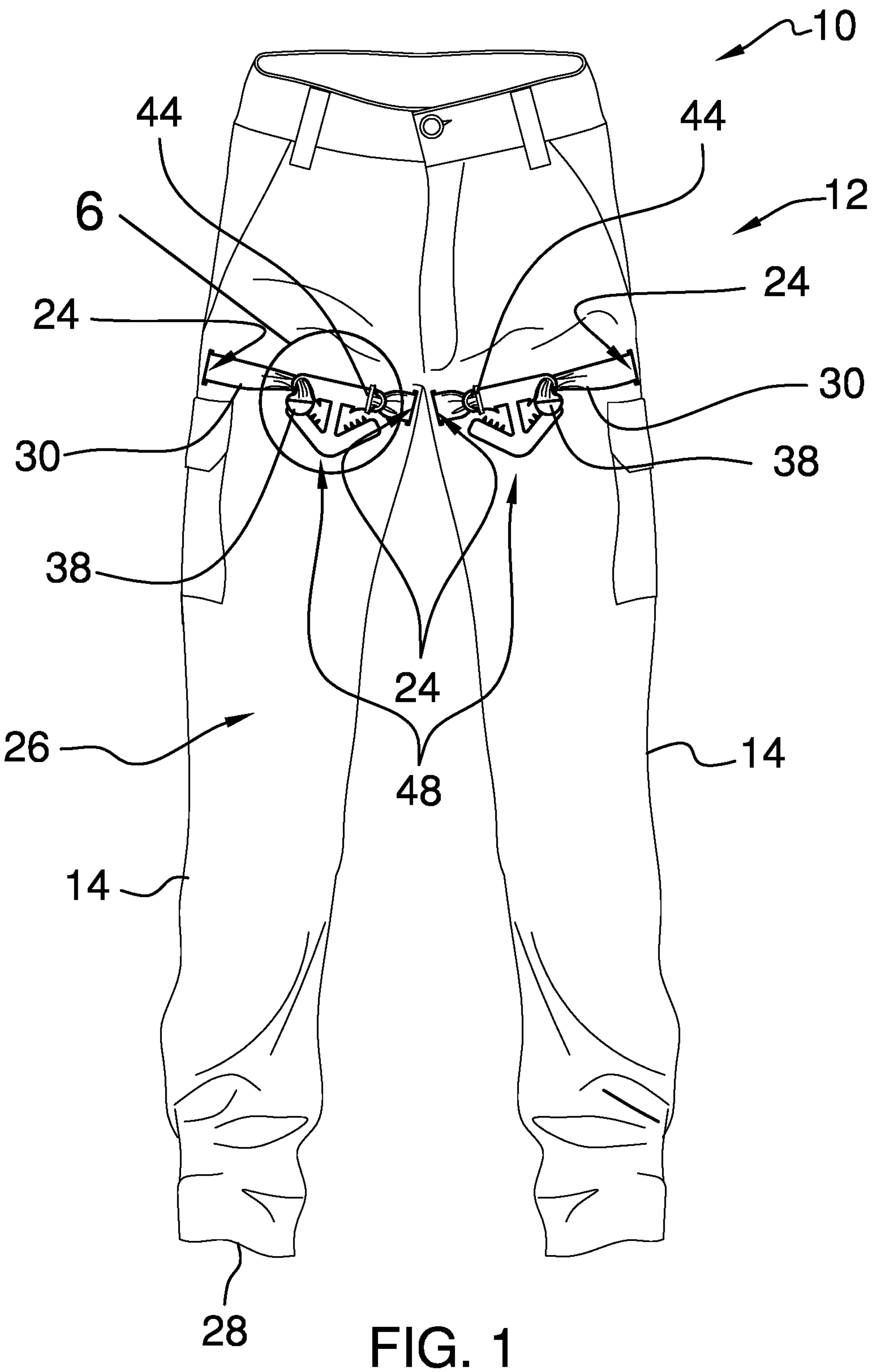
FIG. 1 is a front view of a garment tourniquet device according to an embodiment of the disclosure.
Figure 2:
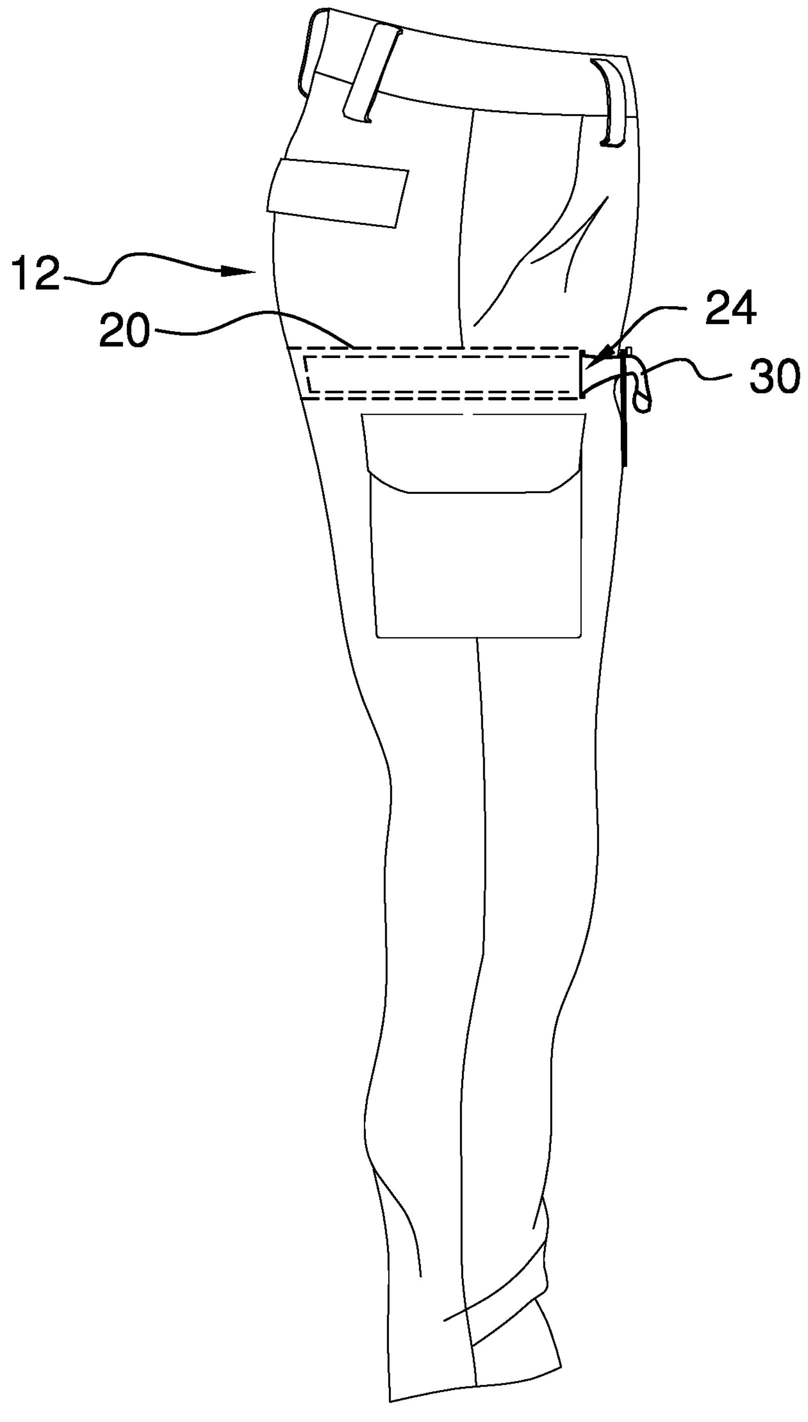
FIG. 2 is a right side phantom view of an embodiment of the disclosure.
Figure 3:
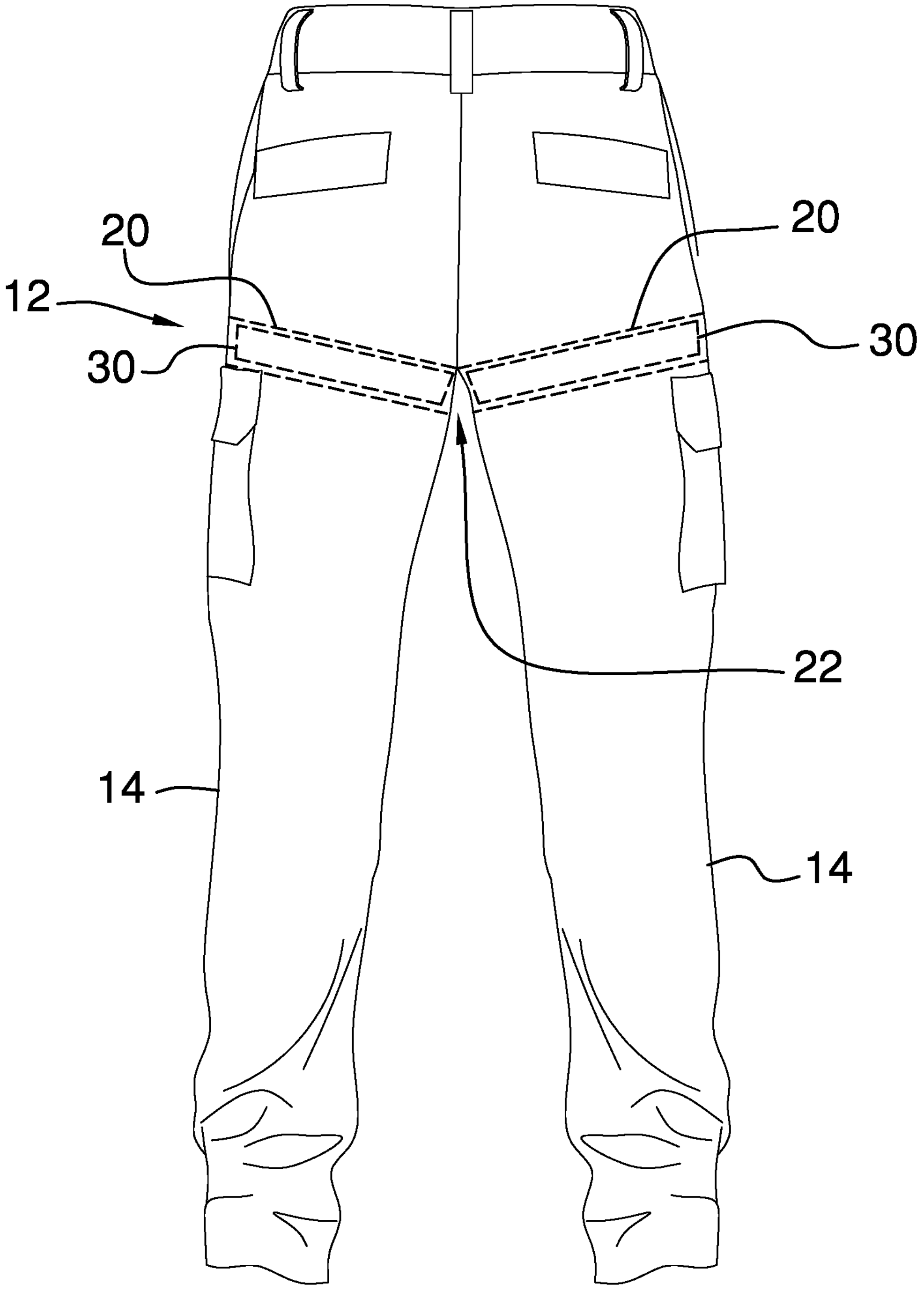
FIG. 3 is a back phantom view of an embodiment of the disclosure.
Figure 4:
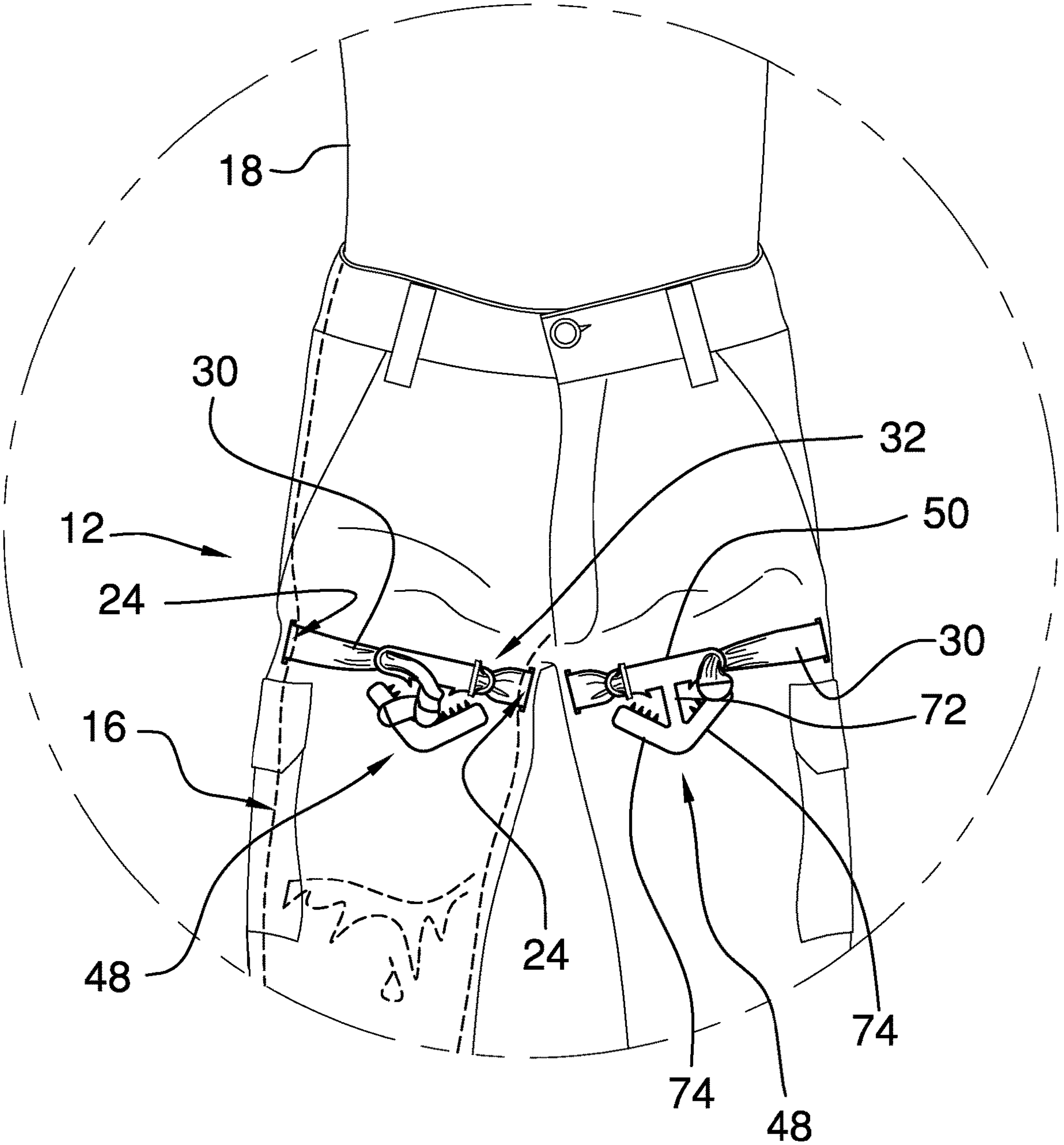
FIG. 4 is a front phantom in-use view of an embodiment of the disclosure.

With reference now to the drawings, and in particular to FIGS. 1 through 6 thereof, a new tourniquet device embodying the principles and concepts of an embodiment of the disclosure and generally designated by the reference numeral 10 will be described.

As best illustrated in FIGS. 1 through 6, the garment tourniquet device 10 generally comprises a pair of pants 12 that has a pair of legs 14 having each of a pair of legs 16 of a user 18 being positioned within a respective one of the pair of legs 14. The pair of pants 12 may comprise pants of military fatigues, pants of an emergency responder's uniform, pants of hunting gear or any other type of pants that would be worn when the user 18 could potentially suffer an injury resulting in arterial bleeding. A pair of channels 20 is each integrated into a respective one of the pair of legs 14 and the channel 20 in each of the pair of legs 14 extends around a substantial diameter of the respective leg 14. Additionally, the channel 20 in each of the pair of legs 14 is positioned adjacent to a crotch 22 of the pair of pants 12.

Each of the pair of legs 14 has a pair of slots 24 which each extend into the channel 20 in a respective one of the pair of legs 14. Each of the pair of slots 24 in each of the pair of legs 14 is positioned on a front side 26 of a respective one of the pair of legs 14 and the pair of slots 24 in each of the pair of legs 14 is spaced apart from each other. Additionally, each of the pair of slots 24 in each of the pair of legs 14 is oriented to extend along a line extending between the crotch 22 of the pair of pants 12 and a cuff 28 of a respective one of the pair of legs 14. Each of the pair of channels 20 may terminate at the pair of slots 24 in the respective leg 14.

A pair of tourniquets 30 is each slidably positioned in the channel 20 in a respective one of the pair of legs 14 of the pair of pants 12. In this way each of the pair of tourniquets 30 is aligned with the femoral artery 32 in a respective one of the user's legs 16 when the user 18 is wearing the pair of pants 12. A respective one of the pair of tourniquets 30 is pullable into a tightened condition to tighten around the femoral artery 32 in the respective user's leg 16 when the user 18 has suffered an injury resulting in arterial bleeding in the user's respective leg 16. In this way the respective tourniquet 30 can inhibit the arterial bleeding in the user's respective leg 16.

Each of the pair of tourniquets 30 has a first end 34 and a second end 36 and each of the pair of tourniquets 30 extends outwardly through the pair of slots 24 in the respective leg 14 of the pair of pants 12. In this way each of the pair of tourniquets 30 forms an open ring having each of the first end 34 and the second end 36 of each of the pair of tourniquets 30 being exposed. Each of the pair of tourniquets 30 is comprised of an elastomeric material thereby facilitating to tourniquets 30 to apply pressure to the femoral artery 32 in the user's respective leg 16 when the respective tourniquet 30 is pulled into the tightened condition.

A pair of stops 38 is provided and each of the pair of stops 38 has a coupled end 40 that is coupled to the first end 34 of a respective one of the pair of tourniquets 30. Additionally, each of the pair of stops 38 has a distal end 42 that is rounded such that each of the pair of stops 38 has a semi-hemispherical shape. A pair of stems 44 is provided which each has an outer surface 46 which is attached to the second end 36 of a respective one of the pair of tourniquets 30. Furthermore, each of the pair of stems 44 is perpendicularly oriented with the respective tourniquet 30.

A pair of clasps 48 is provided and each of the pair of clasps 48 is attached to a respective one of the pair of tourniquets 30 having each of the pair of clasps 48 being exposed on a respective one of the pair of legs 14 of the pair of pants 12. A respective one of the pair of tourniquets 30 is wrapped around the clasp 48 to which the respective tourniquet 30 is attached when the respective tourniquet 30 is pulled into tightened condition for retaining the respective tourniquet 30 in the tightened condition. In this way the respective tourniquet 30 can remain in place for an extended period of time thereby facilitating the user 18 to remain alive until the user 18 can receive medical attention.

Each of the pair of clasps 48 comprises a top member 50 which has a primary end 52, a secondary end 54 and a lower edge 56 extending between the primary end 52 and the secondary end 54. The top member 50 has a first hole 58 extending through a rear surface 60 and a front surface 62 of the top member 50 and the first hole 58 is aligned with the primary end 52. The top member 50 has a second hole 64 extending through the rear surface 60 and the front surface 62 of the top member 50 and the second hole 64 is aligned with the secondary end 54. Additionally, the first end 34 of a respective one of the pair of tourniquets 30 passes through the first hole 58. The stop 38 on the first end 34 of the respective tourniquet 30 inhibits the first end 34 of the respective tourniquet 30 from being pulled rearwardly through the first hole 58 and uncoupling the respective tourniquet 30 from the top member 50. Furthermore, the second end 36 of the respective tourniquet 30 passes through the second hole 64. The stem 44 on the second end 36 of the respective tourniquet 30 rests against the front surface 62 of the top member 50 thereby inhibiting the second end 36 of the respective tourniquet 30 from being pulled rearwardly through the second hole 64 and uncoupling the respective tourniquet 30 from the top member 50.

The top member 50 has a pair of first teeth 66 each extending downwardly from the lower edge 56 and each of the pair of first teeth 66 is spaced from a respective one of the primary end 52 and the secondary end 54. Each of the pair of first teeth 66 has a front end 68 which is perpendicularly oriented with the lower edge 56 and the front end 68 of each of the pair of first teeth 66 is directed toward each other. Each of the pair of first teeth 66 has a back end 70 which slopes between the front end 68 and the lower edge 56 of the top member 50.

Each of the pair of clasps 48 includes a central member 72 which is coupled to and extends downwardly from the lower edge 56 of the top member 50 such that the central member 72 is perpendicularly oriented with the top member 50. Additionally, the central member 72 is centrally positioned between the primary end 52 and the secondary end 54 of the top member 50. The respective tourniquet 30 is wrapped around the central member 72 when the respective tourniquet 30 is pulled into the tightening condition for retaining the respective tourniquet 30 in the tightening condition.

Each of the pair of clasps 48 a pair of lower members 74 which each extends away from the central member 72 in opposite directions from each other such that each of the pair of lower members 74 is spaced downwardly from the top member 50. Furthermore, each of the pair of lower members 74 is oriented to angle upwardly toward the top member 50 such that the central member 72 and the pair of lower members 74 defines an arrow shape. Each the pair of lower members 74 has a plurality of second teeth 76 each extending upwardly from a top edge 78 of a respective one of the lower members 74 such that each of the plurality of second teeth 76 is directed toward the top member 50. The second teeth 76 on each of the pair of lower members 74 are spaced apart from each other and are distributed between the central member 72 and a distal end 80 of the respective lower member 74. In this way the respective tourniquet 30 that is wrapped around the central member 72 is engaged to respective ones of the plurality of second teeth 76 on a respective one of the pair of lower members 74 for inhibiting the respective tourniquet 30 from being unwrapped from the central member 72.

Figure 5:
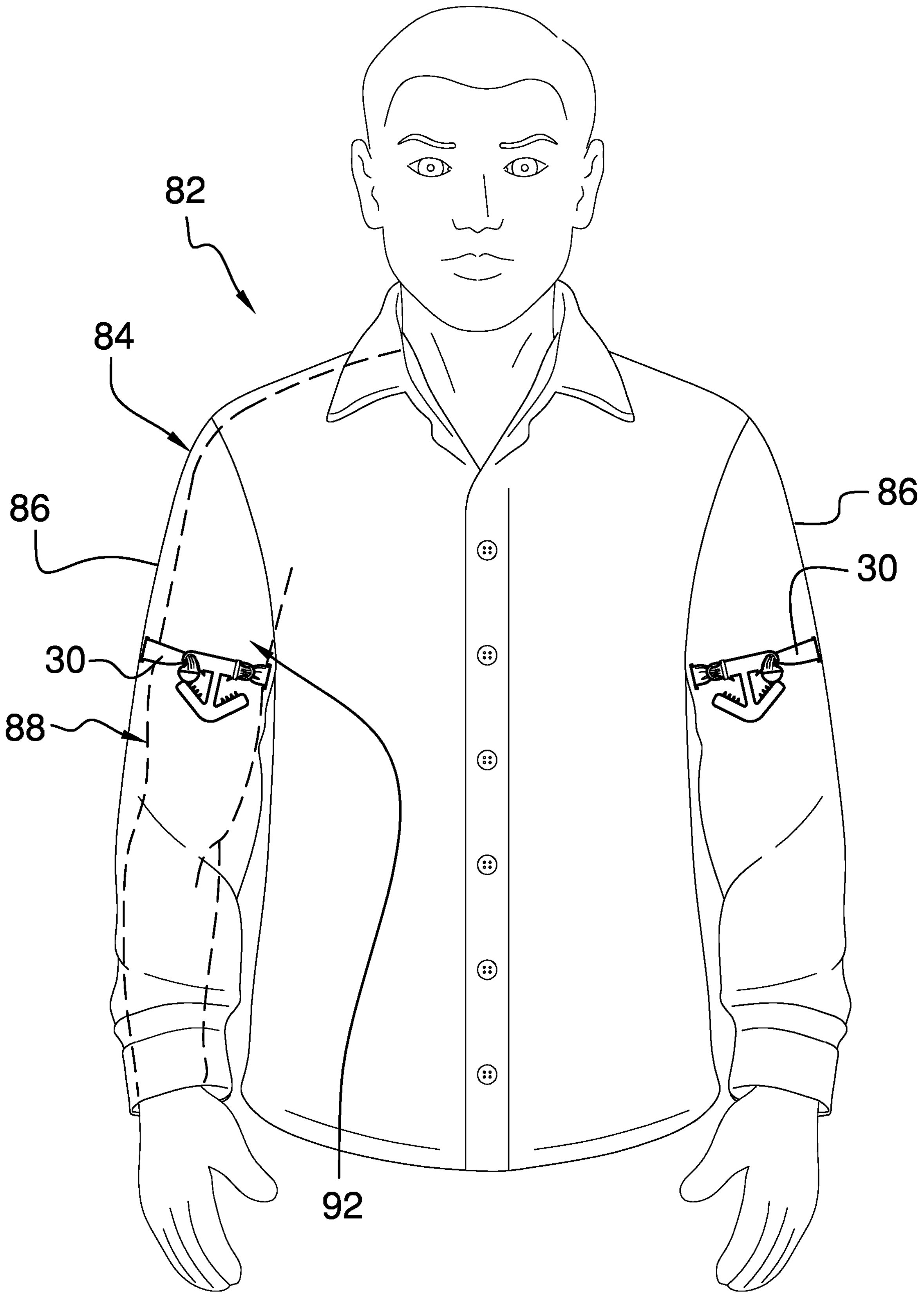
FIG. 5 is a front phantom in-use view of an alternative embodiment of the disclosure.
Figure 6:
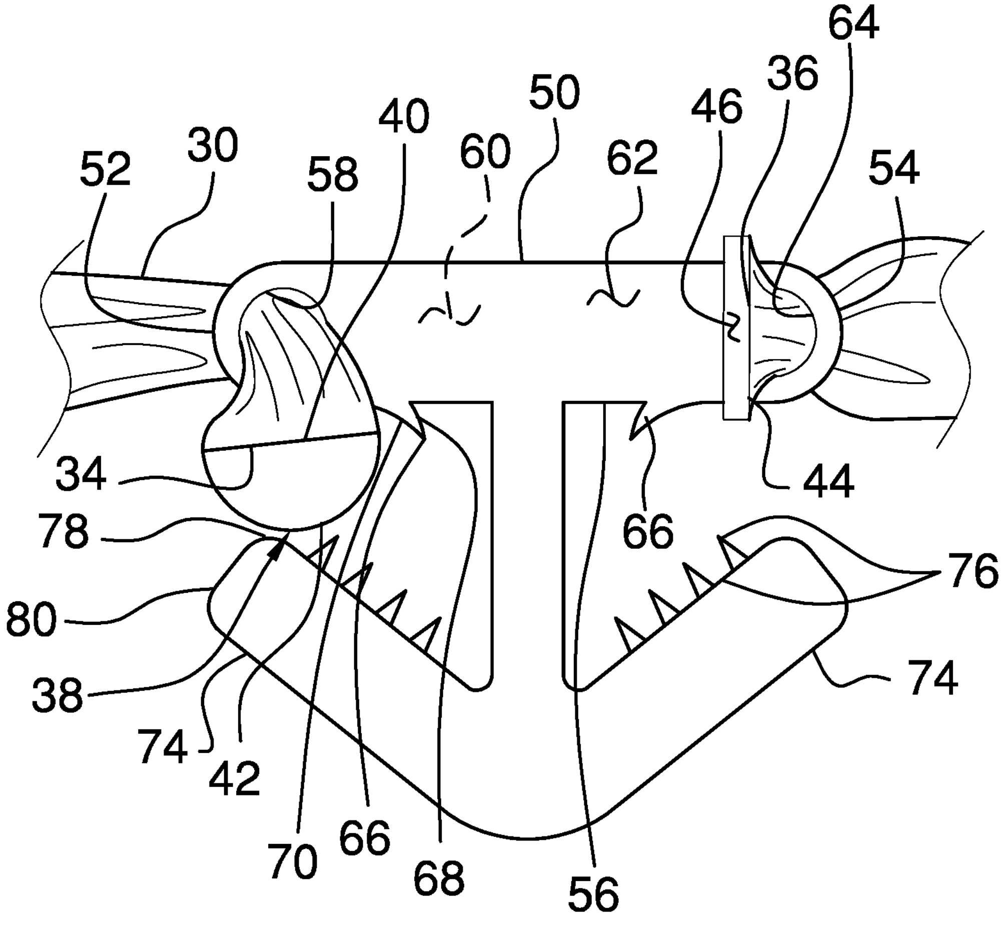
FIG. 6 is a magnified detail view taken from circle 6 of FIG. 1 of an embodiment of the disclosure.

In an alternative embodiment 82 as is shown in FIG. 5, a long sleeved shirt 84 is provided which has a pair of sleeves 86 such that each of the user's arms 88 extends through a respective one of the pair of sleeves 86 when the user 18 is wearing the long sleeved shirt 84. The long sleeved shirt 84 may be the long sleeved shirt of military fatigues, the long sleeved shirt of an emergency responder's uniform, the long sleeved shirt of hunting gear or any other type of long sleeved shirt that would be worn when the user 18 could potentially suffer an injury resulting in arterial bleeding. Each of the pair of channels 20 is integrated into a respective one of the pair of sleeves 86 and each of the channels 20 is positioned adjacent to a connection between the respective sleeve 86 and a torso 90 of the long sleeved shirt 84. In this way each of the pair of tourniquets 30 is aligned with the brachial artery 92 in a respective one of the user's arms 88. Furthermore, a respective one of the tourniquets 30 can tighten around the brachial artery 92 in the respective user's arm 88 when the respective tourniquet 30 is pulled into the tightened condition. Additionally, each of the clasps 48 is positioned on a respective one of the sleeves 86 of the shirt 84.

In use, the first end 34 of a respective one of the tourniquets 30 is pulled to tighten the respective tourniquet 30 around the femoral artery 32 in the respective user's leg 16 when the user 18 experiences an injury in the respective leg 16 that result in arterial bleeding. The respective tourniquet 30 is wrapped around the central member 72 of the respective clasp 48 and the respective tourniquet 30 wrapped around a respective one of the pair of lower members 74 of the respective clasp 48. In this way the respective tourniquet 30 is retained in the tightened condition to compress the femoral artery 32 in the user's respective leg 16 for an extended period of time. Thus, the user 18 can remain alive until the user 18 is able to receive the medial attention necessary to treat the arterial bleeding. The respective tourniquet 30 can be unwrapped from the respective lower member 74 and the central member 72 of the respective clasp 48 at any time by a medical professional that is treating the user's 18 injury to remove the respective tourniquet 30 from the user's respective leg 16.

With respect to the above description then, it is to be realized that the optimum dimensional relationships for the parts of an embodiment enabled by the disclosure, to include variations in size, materials, shape, form, function and manner of operation, device and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A garment tourniquet device having tourniquets being tightenable when a user has been injured thereby inhibiting arterial bleeding, said device comprising:

a pair of pants having a pair of legs wherein said pair of pants is configured to be worn on a user having each of the user's legs being positioned within a respective one of said pair of legs, said pair of pants having a pair of channels each being integrated into each of a respective one of said pair of legs, said channel in each of said pair of legs extending around a substantial diameter of said respective leg;

a pair of tourniquets, each of said pair of tourniquets being positioned in said channel in a respective one of said pair of legs of said pair of pants wherein each of said pair of tourniquets is configured to be aligned with the femoral artery in a respective one of the user's legs when the user is wearing said pair of pants, a respective one of said pair of tourniquets being pullable into a tightened condition wherein said respective tourniquet is configured to tighten around the femoral artery in the respective user's leg when the user has suffered an injury resulting in arterial bleeding in the user's respective leg thereby inhibiting the arterial bleeding in the user's respective leg; and a pair of clasps, each of said pair of clasps being attached to a respective one of said pair of tourniquets having each of said pair of clasps being exposed on a respective one of said pair of legs of said pair of pants, a respective one of said pair of tourniquets being wrapped around said clasp to which said respective tourniquet is attached when said respective tourniquet is pulled into said tightened condition for retaining said respective tourniquet in said tightened condition.

2. The device according to claim 1, wherein:

said channel in each of said pair of legs is positioned adjacent to a crotch of said pair of pants;

each of said pair of legs has a pair of slots which each extend into said channel in a respective one of said pair of legs;

each of said pair of slots in each of said pair of legs is positioned on a front side of a respective one of said pair of legs;

said pair of slots in each of said pair of legs is spaced apart from each other; and each of said pair of slots in each of said pair of legs is oriented to extend along a line extending between said crotch of said pair of pants and a cuff of a respective one of said pair of legs.

3. The device according to claim 2, wherein:

each of said pair of tourniquets has a first end and a second end;

each of said pair of tourniquets extends outwardly through said pair of slots in said respective leg of said pair of pants such that said each of said first end and said second end of each of said pair of tourniquets is exposed; and each of said pair of tourniquets is comprised of an elastomeric material wherein a respective one of said pair of tourniquets is configured to apply pressure to the femoral artery in the user's respective leg when said respective tourniquet is pulled into said tightened condition.

4. The device according to claim 3, wherein:

each of said pair of clasps comprises a top member having a primary end and a secondary end and a lower edge extending between said primary end and said secondary end;

said top member has a first hole extending through a rear surface and a front surface of said top member;

said first hole is aligned with said primary end;

said top member has a second hole extending through said rear surface and said front surface of said top member;

said second hole is aligned with said secondary end;

said first end of a respective one of said pair of tourniquets passes through said first hole; and said second end of said respective tourniquet passes through said second hole.

5. The device according to claim 4, wherein:

said device includes a pair of stops;

each of said pair of stops has a coupled end being coupled to said first end of a respective one of said pair of tourniquets;

each of said pair of stops has a distal end being rounded such that each of said pair of stops has a semi-hemispherical shape; and said stop on said first end of said respective tourniquet inhibits said first end of said respective tourniquet from being pulled rearwardly through said first hole and uncoupling said respective tourniquet from said top member.

6. The device according to claim 4, wherein:

said device includes a pair of stems;

each of said pair of stems has an outer surface being attached to said second end of a respective one of said pair of tourniquets such that each of said pair of stems is perpendicularly oriented with said respective tourniquet; and said stem on said second end of said respective tourniquet rests against said front surface of said top member thereby inhibiting said second end of said respective tourniquet from being pulled rearwardly through said second hole and uncoupling said respective tourniquet from said top member.

7. The device according to claim 4, wherein:

said top member has a pair of first teeth each extending downwardly from said lower edge of said top member;

each of said pair of first teeth is spaced from a respective one of said primary end and said secondary end;

each of said pair of first teeth has a front end which is perpendicularly oriented with said lower edge;

said front end of each of said pair of first teeth is directed toward each other; and each of said pair of first teeth has a back end which slopes between said front end and said lower edge of said top member.

8. The device according to claim 4, wherein:

each of said pair of clasps includes a central member being coupled to and extending downwardly from said lower edge of said top member such that said central member is perpendicularly oriented with said top member; and said central member is centrally positioned between said primary end and said secondary end of said top member.

9. The device according to claim 8, wherein said respective tourniquet is wrapped around said central member when said respective tourniquet is pulled into said tightening condition for retaining said respective tourniquet in said tightening condition.

10. The device according to claim 8, wherein:

each of said pair of clasps includes a pair of lower members;

each of said pair of lower members extends away from said central member in opposite directions from each other such that each of said pair of lower members is spaced downwardly from said top member; and each of said pair of lower members is oriented to angle upwardly toward said top member such that said central member and said pair of lower members defines an arrow shape.

11. The device according to claim 10, wherein:

each said pair of lower members has a plurality of second teeth each extending upwardly from a top edge of a respective one of said lower members such that each of said plurality of second teeth is directed toward said top member; and said plurality of second teeth on each of said pair of lower members is spaced apart from each other and is distributed between said central member and a distal end of said respective lower member such that said respective tourniquet that is wrapped around said central member is engaged to respective ones of said plurality of second teeth on a respective one of said pair of lower members for inhibiting said respective tourniquet from being unwrapped from said central member.

12. A garment tourniquet device having tourniquets being tightenable when a user has been injured thereby inhibiting arterial bleeding, said device comprising:

a pair of pants having a pair of legs wherein said pair of pants is configured to be worn on a user having each of the user's legs being positioned within a respective one of said pair of legs, said pair of pants having a pair of channels each being integrated into a respective one of said pair of legs, said channel in each of said pair of legs extending around a substantial diameter of said respective leg, said channel in each of said pair of legs being positioned adjacent to a crotch of said pair of pants, each of said pair of legs having a pair of slots which each extend into said channel in a respective one of said pair of legs, each of said pair of slots in each of said pair of legs being positioned on a front side of a respective one of said pair of legs, said pair of slots in each of said pair of legs being spaced apart from each other, each of said pair of slots in each of said pair of legs being oriented to extend along a line extending between said crotch of said pair of pants and a cuff of a respective one of said pair of legs;

a pair of tourniquets, each of said pair of tourniquets being positioned in said channel in a respective one of said pair of legs of said pair of pants wherein each of said pair of tourniquets is configured to be aligned with the femoral artery in a respective one of the user's legs when the user is wearing said pair of pants, a respective one of said pair of tourniquets being pullable into a tightened condition wherein said respective tourniquet is configured to tighten around the femoral artery in the respective user's leg when the user has suffered an injury resulting in arterial bleeding in the user's respective leg thereby inhibiting the arterial bleeding in the user's respective leg, each of said pair of tourniquets having a first end and a second end, each of said pair of tourniquets extending outwardly through said pair of slots in said respective leg of said pair of pants such that said each of said first end and said second end of each of said pair of tourniquets is exposed, each of said pair of tourniquets being comprised of an elastomeric material wherein a respective one of said pair of tourniquets is configured to apply pressure to the femoral artery in the user's respective leg when said respective tourniquet is pulled into said tightened condition;

a pair of stops, each of said pair of stops having a coupled end being coupled to said first end of a respective one of said pair of tourniquets, each of said pair of stops having a distal end being rounded such that each of said pair of stops has a semi-hemispherical shape;

a pair of stems, each of said pair of stems having an outer surface being attached to said second end of a respective one of said pair of tourniquets such that each of said pair of stems is perpendicularly oriented with said respective tourniquet;

a pair of clasps, each of said pair of clasps being attached to a respective one of said pair of tourniquets having each of said pair of clasps being exposed on a respective one of said pair of legs of said pair of pants, a respective one of said pair of tourniquets being wrapped around said clasp to which said respective tourniquet is attached when said respective tourniquet is pulled into said tightened condition for retaining said respective tourniquet in said tightened condition, each of said pair of clasps comprising:

a top member having a primary end and a secondary end and a lower edge extending between said primary end and said secondary end, said top member having a first hole extending through a rear surface and a front surface of said top member, said first hole being aligned with said primary end, said top member having a second hole extending through said rear surface and said front surface of said top member, said second hole being aligned with said secondary end, said first end of a respective one of said pair of tourniquets passing through said first hole, said stop on said first end of said respective tourniquet inhibiting said first end of said respective tourniquet from being pulled rearwardly through said first hole and uncoupling said respective tourniquet from said top member, said second end of said respective tourniquet passing through said second hole, said stem on said second end of said respective tourniquet resting against said front surface of said top member thereby inhibiting said second end of said respective tourniquet from being pulled rearwardly through said second hole and uncoupling said respective tourniquet from said top member;

wherein said top member has a pair of first teeth each extending downwardly from said lower edge, each of said pair of first teeth being spaced from a respective one of said primary end and said secondary end, each of said pair of first teeth having a front end which is perpendicularly oriented with said lower edge, said front end of each of said pair of first teeth being directed toward each other, each of said pair of first teeth having a back end which slopes between said front end and said lower edge of said top member;

a central member being coupled to and extending downwardly from said lower edge of said top member such that said central member is perpendicularly oriented with said top member, said central member being centrally positioned between said primary end and said secondary end of said top member;

wherein said respective tourniquet is wrapped around said central member when said respective tourniquet is pulled into said tightening condition for retaining said respective tourniquet in said tightening condition;

a pair of lower members, each of said pair of lower members extending away from said central member in opposite directions from each other such that each of said pair of lower members is spaced downwardly from said top member, each of said pair of lower members being oriented to angle upwardly toward said top member such that said central member and said pair of lower members defines an arrow shape; and wherein each said pair of lower members has a plurality of second teeth each extending upwardly from a top edge of a respective one of said lower members such that each of said plurality of second teeth is directed toward said top member, said plurality of second teeth on each of said pair of lower members being spaced apart from each other and being distributed between said central member and a distal end of said respective lower member such that said respective tourniquet that is wrapped around said central member is engaged to respective ones of said plurality of second teeth on a respective one of said pair of lower members for inhibiting said respective tourniquet from being unwrapped from said central member.

13. The device according to claim 12, wherein:

said device includes a shirt having a pair of sleeves wherein said shirt is configured to be worn on the user having each of the user's arms extending through a respective one of said pair of sleeves;

each of said pair of channels is integrated into a respective one of said pair of sleeves;

each of said pair of channels is positioned adjacent to a connection between said respective sleeve and a torso of said shirt wherein each of said pair of tourniquets is configured to be aligned with the brachial artery in a respective one of the user's arms thereby facilitating a respective one of said tourniquets to tighten around the brachial in the respective user's arm when said respective tourniquet is pulled into said tightened condition.

* * * * *